(12) United States Patent
Briot et al.

(10) Patent No.: US 7,504,548 B2
(45) Date of Patent: Mar. 17, 2009

(54) METHOD FOR FORMULATION OF SYNTHETIC GAS OILS OR ADDITIVES FOR GAS OIL

(75) Inventors: Patrick Briot, Pommier de Beaurepaire (FR); Sylvie Lacombe, Saint Genis Laval (FR); Jean-François Joly, Lyons (FR); Eric Llido, Communay (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 651 days.

(21) Appl. No.: 10/943,896

(22) Filed: Sep. 20, 2004

(65) Prior Publication Data

US 2005/0065388 A1 Mar. 24, 2005

(30) Foreign Application Priority Data

Sep. 19, 2003 (FR) .................................. 03 11033

(51) Int. Cl.
*C07C 2/64* (2006.01)
*C10G 35/00* (2006.01)
(52) U.S. Cl. ........................ 585/455; 208/133; 208/142
(58) Field of Classification Search ................. 585/585; 208/133, 142
See application file for complete search history.

(56) References Cited

U.S. PATENT DOCUMENTS

| | | | |
|---|---|---|---|
| 4,066,531 A | * | 1/1978 | Owen et al. ............... 208/120.1 |
| 4,447,312 A | | 5/1984 | Angevine et al. |
| 4,594,143 A | | 6/1986 | Tabak |
| 4,992,607 A | | 2/1991 | Harandi et al. |
| 5,705,724 A | | 1/1998 | Collins et al. |

FOREIGN PATENT DOCUMENTS

WO WO 00/39253 A 7/2000

* cited by examiner

*Primary Examiner*—Thuan Dinh Dang
(74) *Attorney, Agent, or Firm*—Millen, White, Zelano & Branigan, P.C.

(57) ABSTRACT

The invention relates to a method for formulation of a synthetic gas oil or an additive for gas oil in which an alkyl-aromatic compound or a mixture of alkyl-aromatic compounds is selected based on at least one parameter that is selected from the group that consists of the number of cycles of the aromatic core, the number of alkyl chains that are grafted to the aromatic cycle, the length of the alkyl chain or chains, the position of the aromatic cycle or cycles on the alkyl chain or chains of said alkyl-aromatic compound or compounds such that the cetane number of the synthetic gas oil or the additive for gas oil is greater than 30. The invention also relates to a process for the production of alkyl-aromatic compounds for use as a gas oil or additive.

19 Claims, No Drawings

METHOD FOR FORMULATION OF SYNTHETIC GAS OILS OR ADDITIVES FOR GAS OIL

This relates to the field of gas oil or base production that can be part of the composition of a gas oil.

Because of the current rapid expansion of the number of diesel vehicles on the road in most industrialized countries, the current world market of hydrocarbons notes a deficit in gas oil and an excess in gasoline relative to the available proportions of the refinery output. This imbalance is in large part due to the fact that the amounts of each fraction obtained are linked to the initial composition of the crude oil to be treated and that few processes currently make possible a certain degree of refinery output flexibility of the ratio by weight of gasoline/gas oil.

By way of example, in France, taking into account the necessity of meeting the demand for gas oil, the excess gasoline produced in 2002 would be on the order of 17 million tons.

One of the objects of this invention is to provide an alternative solution that makes it possible to select certain compounds that can constitute a gas oil or a base (additive) for gas oil and more particularly whose cetane number (IC) satisfies current standards, i.e., having an IC that is equal to or greater than 45. Another object of this invention is to provide a solution that makes it possible to modify the gasoline/gas oil ratio of the refinery output by selecting and by modifying, in a simple and economic manner, certain components of the gasoline so as to constitute an acceptable gas oil or an acceptable base for gas oil.

More particularly, the invention relates to a method for formulation of a synthetic gas oil or an additive for gas oil in which an alkyl-aromatic compound or a mixture of alkyl-aromatic compounds is selected based on at least one parameter that is selected from the group that consists of the number of cycles of the aromatic core, the number of alkyl chains grafted to the aromatic cycle, the length of the alkyl chain or chains, the position of the aromatic cycle or cycles on the alkyl chain or chains of said alkyl-aromatic compound or compounds, such that the cetane number of the synthetic gas oil or the additive for gas oil is greater than 30. Said cetane number preferably will be greater than 35 and very preferably greater than 40, and even 45.

For example, the alkyl-aromatic compound or compounds can be selected based on the combination of at least two of the preceding parameters, or else based on the combination of all of the preceding pararmeters.

Most often, the aromatic core is a benzene core, such that the selection is carried out on at least one parameter that is selected from the group that consists of the number of alkyl chains that are grafted to the aromatic cycle, the length of the alkyl chain or chains, the position of the aromatic cycle or cycles on the alkyl chain or chains of said alkyl-aromatic compound or compounds, preferably on all of said parameters.

The invention also relates to a process for the production of alkyl-aromatic compounds for use as gas oil or as an additive for gas oil in which said alkyl-aromatic compound or compounds are synthesized by reaction of a feedstock that comprises aromatic compounds with alkylating agents, whereby said alkylating agents are selected based on the number of cycles of the aromatic core and/or the number of alkyl chains that are grafted to the aromatic cycle and/or the length of the alkyl chain or chains and/or the position of the aromatic cycle or cycles on the alkyl chain or chains of said alkyl-aromatic compound or compounds that are finally obtained.

According to one of the possible embodiments of the invention, the cetane number is improved to be brought to a value of greater than 30, preferably greater than 35, very preferably greater than 40, and even 45 after a final stage of at least partial hydrogenation of at least a portion of the alkyl-aromatic compound or of the mixture of alkyl-aromatic compounds that is contained in said gas oil or said additive for gas oil.

According to one of the possible embodiments of the invention, said gas oil or said additive is synthesized by an alkylation reaction of a feedstock that is obtained from a gasoline, said feedstock comprising benzene and/or one or more alkyl-aromatic compounds and whose distillation interval is between about 60 and about 180° C., preferably between 80 and 180° C.

For example, said hydrocarbon feedstock is obtained by distillation between about 60° C. and about 180° C. of a gasoline that is obtained from a catalytic cracking process. According to another example, said hydrocarbon feedstock is obtained from a catalytic reforming process.

Preferably, in the two preceding cases, said distillation interval is advantageously encompassed between about 80° C. and about 120° C. The applicant actually found that high-quality gas oils were obtained by reaction of the distillate obtained in this distillation range with reagents preferably containing alkyl groups containing 7 to 14 carbon atoms. Actually, the cetane number of these gas oils met current standards, without recourse to total or partial hydrogenation of the aromatic cycles.

In particular, certain alkylates of the benzene, i.e., of a benzene core of which one or two hydrogen atoms have been substituted by partially or totally hydrogenated aliphatic and/or alkyl-benzene chains (alkyl-cyclohexadiene, alkyl-cyclohexene, alkyl-cyclohexane), can be part of the composition, in large proportions, of the synthetic gas oil that is obtained by application of the method according to this invention.

Certain compounds that can be part of the composition of said synthetic gas oil can also have the following generic formula:

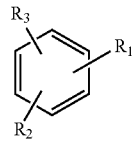

FORMULA A

In this case, substituents R1 and R2 can be either only a hydrogen atom or an alkyl chain that comprises, for example, one to three carbon atoms. Chain R3 can contain, for example, between 5 and 25 carbon atoms, and even between 6 and 23 carbon atoms, or even between 7 and 20 carbon atoms.

These compounds are prepared by, for example, alkylation, by olefins or alkyl halides, of aromatic compounds (for example, benzene, alkyl-benzenes or alkyl-xylenes) that are obtained from the fractionation of a gasoline fraction. However, it preferably will be possible not to select certain alkyl-xylenes that have a cetane number of less than 30. At the very least, they will not be used alone, but rather mixed with other compounds such as alkylbenzenes.

Finally, the invention relates to the use of an alkyl-aromatic compound or a mixture of alkyl-aromatic compounds for the production of a synthetic gas oil or a gas oil additive whose cetane number is greater than 30 in which said alkyl-aromatic compound or compounds are selected based on at least one parameter that is selected from the group that consists of the number of cycles of the aromatic core, the number of alkyl chains that are grafted to the aromatic cycle, the length of the alkyl chain or chains, the position of the aromatic cycle or cycles on the alkyl chain or chains of said alkyl-aromatic compound or compounds.

The following examples illustrate the method, the process and the use that are the object of this application but in no way limit the extent of the latter.

EXAMPLE 1

An excess of benzene is created with bromo-1 hexane in a flask that is topped with a coolant. Aluminum chloride (AlCl3) is added to the mixture. This mixture is heated to 80° C. while being stirred. This reaction is well known under the name of Friedel and Craft. The products of the reaction are, on the one hand, unreacted benzene, because it is in excess, and, on the other hand, phenyl-1 hexane (or according to formula A: R1=R2=hydrogen, R2=normal hexyl). The excess benzene is eliminated by distillation. The cetane number of the compound that is obtained was measured according to a technique that is well known to one skilled in the art. The cetane number is 26.

EXAMPLE 2

An excess of benzene is created with bromo-1 decane in the same device as the one that is described in Example 1. Aluminum chloride (AlCl3) is added to the mixture. This mixture is heated to 80° C. while being stirred. The products of the reaction are, on the one hand, unreacted benzene, because it is in excess, and, on the other hand, phenyl-1 decane (R1=R2=H, R3=normal decyl). The benzene is eliminated by distillation. The cetane number of the compound that is obtained has been measured according to a technique that is well known to one skilled in the art. The cetane number of the product that is finally obtained is 50.

EXAMPLE 3

An excess of benzene is created with bromo-1 dodecane in a flask that is topped with a coolant. Aluminum chloride (AlCl3) is added to the mixture. This mixture is heated to 80° C. while being stirred. The products of the reaction are, on the one hand, unreacted benzene, because it is in excess, and, on the other hand, phenyl-1 dodecane (R1=R2=H, R3=normal dodecyl). The benzene is eliminated by distillation. The cetane number of the product that is finally obtained is 68.

EXAMPLE 4

An excess of a mixture of xylene that comprises 52.3% of meta-xylene, 16.1% of para-xylene and 31.6% of ortho-xylene is created with bromo-1 octane in a flask that is topped with a coolant. Aluminum chloride (AlCl3) is added to the mixture. This mixture is heated to 80° C. while being stirred. The products of the reaction are, on the one hand, the mixture of xylenes that has not reacted, because it is in excess, and compounds comprising a xylenyl group (meta, para or ortho) that is substituted in n-position (n=1 to 4) on the octane molecule (or according to formula A: R1=R2=methyl, R3=octyl normal group attached to the aromatic core by one of the octyl chain carbons). The benzene is eliminated by distillation. The cetane number of the finally obtained product is 20.

EXAMPLE 5

An excess of benzene is mixed with octene-1. The molar ratio of benzene to olefin is equal to 10 mol/mol. This mixture is sent into a reactor that contains a catalyst that consists of 80% by weight of mordenite-type zeolite and 20% by weight of alumina. This catalyst is heated to 140° C. The volumetric flow rate of feedstock relative to the volume of catalyst is equal to 1 liter/liter.hour.

The effluents at the outlet of the reactor consist of unreacted benzene and a mixture of different isomers of the phenyl-n octane (phenyl that is substituted in n-position on the octane chain) that consists of 85% by weight of phenyl-2 octane (R1=R3=hydrogen and R2=normal octyl attached by its $2^{nd}$ carbon to the aromatic core). The benzene is eliminated by distillation. The cetane number of the product that is finally obtained is 32.

EXAMPLE 6

In the same device as in Example 5, the feedstock consists of benzene and undecene-1. The operating conditions are identical to those of Example 5 except for the reaction temperature, which is equal to 155° C. The effluents at the outlet of the unit consist of benzene and a mixture of different phenyl-n undecane isomers, including 84% by weight of phenyl-2 undecane (or according to formula A: R1=R2=H and R3=normal undecyl attached by its $2^{nd}$ carbon to the aromatic core). The cetane number of the product that is finally obtained is 51.

EXAMPLE 7

In the same device as in Example 5, the feedstock consists of benzene and 1-tetradecene. The operating conditions are identical to those of Example 5 except for the temperature, which is equal to 160° C. The effluents at the outlet of the unit consist of benzene and a mixture of various isomers of the phenyl-n tetradecane type, including 84% by weight of phenyl-2 tetradecane (or according to formula A: R1=R2=H and R3=normal tetradecyl attached by its $2^{nd}$ carbon to the aromatic core). The cetane number of the product that is finally obtained is 49.

EXAMPLE 8

The same device as in Example 5 was used. The catalyst is a catalyst that contains 80% by weight of zeolite Y and 20% by weight of alumina. The feedstock is a mixture of benzene and dodecene-1. The molar ratio of benzene to olefin is equal to 10 mol/mol. The ratio of the volumetric flow rate of feedstock to the volume of catalyst is equal to 1 liter/liter.hour.

The temperature of the catalyst is equal to 150° C. The effluents at the outlet of the unit consist of benzene that has not reacted and a mixture of various phenyl dodecane isomers. The benzene is eliminated by distillation. The phenyl-n dodecanes consist of an approximately equimolar mixture of different isomers: phenyl-2 dodecane (25%), phenyl-3 dodecane (20%), phenyl-4 dodecane (18%), phenyl-5 dodecane (19%), phenyl-6 dodecane (18%) (or according to formula A: R1=R2=H and R3=normal dodecyl attached respectively via carbons of rank 2 to 6 to the aromatic core). The cetane number of the isomer mixture that is finally obtained is 42.

EXAMPLE 9

The same device as in Example 5 was used. The catalyst, as in Example 8, is a catalyst that contains 80% by weight of Y zeolite and 20% by weight of alumina. The feedstock is a mixture of benzene and 1-eicosene. The molar ratio of benzene to olefin is equal to 10 mol/mol. The ratio of the volumetric flow rate of feedstock to the volume of catalyst is equal to 1 liter/liter.hour. The temperature of the catalyst is equal to 165° C.

The effluents at the outlet of the unit consist of benzene that has not reacted and a mixture of various phenyl-n eicosane-type isomers (or according to formula A: R1=R2=H and R3=normal eicosyl attached by its nth carbon to the aromatic core). The cetane number of the mixture of isomers that is finally obtained is 39.

The comparison of the cetane numbers of the compounds or compositions of Examples 1 to 9 shows that by applying the method that is described in Claim 1, it is possible to make an effective selection of certain compounds or certain groups of compounds and even to modify the composition of a mixture of hydrocarbons so as to modify the cetane number thereof in particular for the purpose of using it as gas oil or as a base for gas oil, whereby said modulation can relate in particular to:

a) the number of aromatic cycles,
b) the number of substituents, i.e., the alkyl chain, on the aromatic cycle,
c) the length of the alkyl chain or chains that are grafted to the cycle or cycles,
d) the position of the aromatic cycle or cycles on the paraffinic chain.

EXAMPLE 10

The mixture of phenyl-n tetradecane-type isomers that is obtained in Example 7 is hydrogenated on a catalyst with a palladium base deposited on carbon under 5 MPa of hydrogen at 250° C. The product that is obtained at the end of this hydrogenation is an isomer mixture that contains primarily cyclohexyl-2 tetradecane.

EXAMPLE 11

The mixture of phenyl-n eicosane-type isomers that is obtained in Example 9 is hydrogenated on palladium-based catalyst that is deposited on carbon under 5 MPa of hydrogen at 250° C.

The product that is obtained at the end of this hydrogenation is a cyclohexyl-n eicosane-type isomer mixture.

The cetane number after hydrogenation has been measured. The results that are obtained are presented in Table 1.

TABLE 1

Cetane Number of Aromatic Alkylates Before and After Hydrogenation

| Compounds | Cetane |
|---|---|
| Phenyl-n tetradecane (before hydrogenation) - Example 7 | 49 |
| Cyclohexyl-n tetradecane (after hydrogenation) - Example 10 | 57 |
| Phenyl-n eicosane (before hydrogenation) - Example 9 | 39 |
| Cyclohexyl-n eicosane (after hydrogenation) - Example 11 | 66 |

Examples 10 and 11 make it possible to show that the total or partial hydrogenation of the aromatic cycle makes it possible to improve the cetane number of these compounds, thus making it possible to reach the required standards.

The invention claimed is:

1. A process for the production of a synthetic gas oil or an additive for gas oil from a gasoline fraction feedstock having a distillation interval of between about 80° and about 120° C. and fractionated from a parent gasoline, wherein alkyl-aromatic compounds are synthesized by alkylation reaction of said gasoline fraction feedstock having a distillation interval between about 80° and about 120° C., said feedstock comprising benzene and/or one or more alkyl-aromatic compounds said alkyl-aromatic compounds being only those having a distillation interval between about 80° and 120° C., said alkylation being conducted with alkylating agents selected based on the number of cycles of the aromatic core and/or the number of alkyl chains that are grafted to the aromatic cycle and/or the length of the alkyl chain or chains and/or the position of the aromatic cycle or cycles on the alkyl chain or chains of said alkyl-aromatic compound or compounds that are finally obtained, such that the cetane number of the synthetic gas oil or the additive for the gas oil is greater than 30, and in which at least one alkyl chain that is grafted to the aromatic cycle comprises between 7 and 20 carbon atoms.

2. A process according to claim 1, in which the cetane number of greater than 30 is obtained after a final stage of at least partial hydrogenation of at least a portion of the alkyl-aromatic compound or of the mixture of alkyl-aromatic compounds contained in said gas oil or said additive for gas oil.

3. A process according to claim 2, in which said gasoline fraction is obtained by distillation of parent gasoline obtained from a catalytic cracking process.

4. A process according to claim 1, in which the feedstock comprises benzene.

5. A process according to claim 1, in which said hydrocarbon feedstock is obtained from a catalytic reforming process.

6. A process according to claim 1, in which said at least one alkyl chain that is grafted to the aromatic cycle comprises between 7 and 14 carbon atoms.

7. A process according to claim 1, wherein the cetane number is greater than 35.

8. A process according to claim 1, wherein the cetane number is greater than 40.

9. A process according to claim 1, wherein the cetane number is greater than 45.

10. A process according to claim 4, wherein said at least one alkyl chain grafted to the aromatic cycle consists essentially of 11 carbon atoms.

11. A process according to claim 4, wherein said at least one alkyl chain grafted to the aromatic cycle consists essentially of 12 carbon atoms.

12. A process according to claim 1, further comprising an initial step of fractionating said parent gasoline to obtain said gasoline fraction.

13. A process according to claim 2, further comprising an initial step of fractionating said parent gasoline to obtain said gasoline fraction.

14. A process according to claim 3, further comprising an initial step of fractionating said parent gasoline to obtain said gasoline fraction.

15. A process according to claim 7, further comprising an initial step of fractionating said parent gasoline to obtain said gasoline fraction.

16. A process according to claim 4, further comprising an initial step of fractionating said parent gasoline to obtain said gasoline fraction.

17. A process according to claim 5, further comprising an initial step of fractionating said parent gasoline to obtain said gasoline fraction.

18. A process according to claim 9, further comprising an initial step of fractionating said parent gasoline to obtain said gasoline fraction.

19. A process according to claim 11, further comprising an initial step of fractionating said parent gasoline to obtain said gasoline fraction.

* * * * *

UNITED STATES PATENT AND TRADEMARK OFFICE
CERTIFICATE OF CORRECTION

| | | |
|---|---|---|
| PATENT NO. | : 7,504,548 B2 | Page 1 of 1 |
| APPLICATION NO. | : 10/943896 | |
| DATED | : March 17, 2009 | |
| INVENTOR(S) | : Patrick Briot | |

It is certified that error appears in the above-identified patent and that said Letters Patent is hereby corrected as shown below:

On the title page, item [75] Inventors: line 3, reads "Lyons" should read -- Lyon --

Signed and Sealed this

Sixteenth Day of June, 2009

JOHN DOLL
*Acting Director of the United States Patent and Trademark Office*